United States Patent [19]

Nilsson et al.

[11] Patent Number: 5,286,454
[45] Date of Patent: Feb. 15, 1994

[54] CUVETTE

[76] Inventors: Sven-Erik Nilsson, Döbeliusvägen 39, S-253 67 Helsingborg; Jan Lilja, Södra Brunnsvägen 63, S-253 68 Helsingborg, both of Sweden

[21] Appl. No.: 768,321
[22] PCT Filed: Apr. 25, 1990
[86] PCT No.: PCT/SE90/00275
§ 371 Date: Oct. 17, 1991
§ 102(e) Date: Oct. 17, 1991
[87] PCT Pub. No.: WO90/13016
PCT Pub. Date: Nov. 1, 1990

[30] Foreign Application Priority Data

Apr. 26, 1989 [SE] Sweden ............ 8911518

[51] Int. Cl.⁵ .................................. B01L 3/00
[52] U.S. Cl. ........................... 422/102; 422/101; 422/72; 422/58; 422/57; 436/177; 436/178
[58] Field of Search ............ 422/102, 72, 57, 58, 422/101; 436/45, 177, 178, 180, 809; 356/246; 494/16-21, 45; 210/206; 435/287, 291, 301, 311

[56] References Cited

U.S. PATENT DOCUMENTS

| | | | |
|---|---|---|---|
| 1,365,183 | 1/1921 | Moffatt | 422/102 |
| 3,795,451 | 3/1974 | Mailen | 422/72 |
| 3,799,742 | 3/1974 | Coleman | 356/246 |
| 3,901,658 | 8/1975 | Burtis et al. | 422/72 |
| 4,066,512 | 1/1978 | Lai et al. | 435/10 |
| 4,088,448 | 5/1978 | Lilja | 422/57 |
| 4,178,345 | 12/1979 | Terk | 435/287 |
| 4,284,602 | 8/1981 | Kelton et al. | 356/246 |
| 4,330,206 | 5/1982 | Gausmann et al. | 356/246 |
| 4,447,546 | 5/1984 | Hirschfeld | 422/57 |
| 4,462,964 | 7/1984 | Guigan | 422/61 |
| 4,605,536 | 8/1986 | Kuhnert et al. | 422/58 |
| 4,654,197 | 3/1987 | Lilja et al. | 422/58 |
| 4,696,798 | 9/1987 | Timgren | 422/102 |
| 4,714,590 | 12/1987 | Guigan | 422/102 |
| 4,756,884 | 7/1988 | Hillman et al. | 422/81 |
| 4,806,316 | 2/1989 | Johnson et al. | 422/58 |
| 4,883,763 | 11/1989 | Holen et al. | 422/102 |
| 4,999,304 | 3/1991 | Robertson | 436/177 |
| 5,039,617 | 8/1991 | McDonald et al. | 422/58 |

Primary Examiner—Robert J. Warden
Assistant Examiner—Hien Tran
Attorney, Agent, or Firm—Kane, Dalsimer, Sullivan, Kurucz, Levy, Eisele and Richard

[57] ABSTRACT

A cuvette for taking up a fluid and mixing the fluid with a reagent for analyzing the mixture consists of a body (10) of glass or polymeric material having a first cavity (12) in which the fluid can be taken up, preferably by capillary action, through an inlet (13), and at least one further cavity (21) exerting capillary force on fluid which is transported from the first cavity (12) into a reception cavity (17) by subjecting the cuvette to centrifugal force. The further cavity (21) preferably exerts capillary force through a wick (19) which does not extend as far as the bottom of the reception cavity (17), and a capillary channel (20). In those cases where more than one further cavity (21) is provided, each such cavity (21) communicates with a further reception cavity into which the fluid can be transported from the cavity (21) by the exertion of centrifugal force. The cuvette may also have cavities for receiving washing or diluting liquid, which are connected in series or in parallel with the cavity (12).

17 Claims, 2 Drawing Sheets

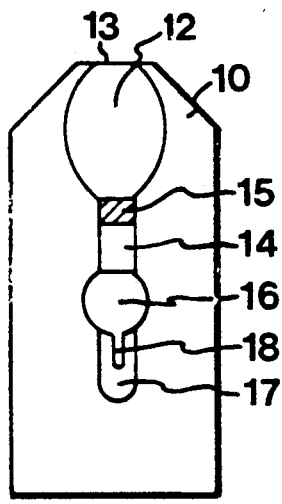
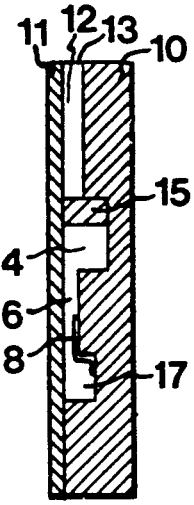
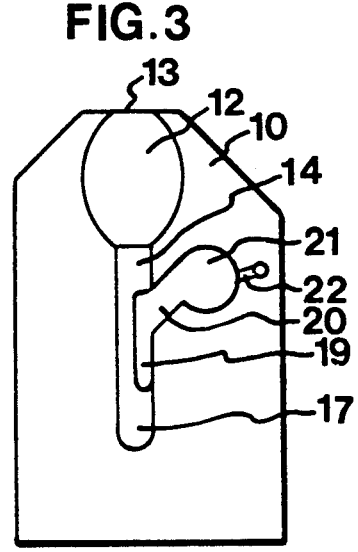
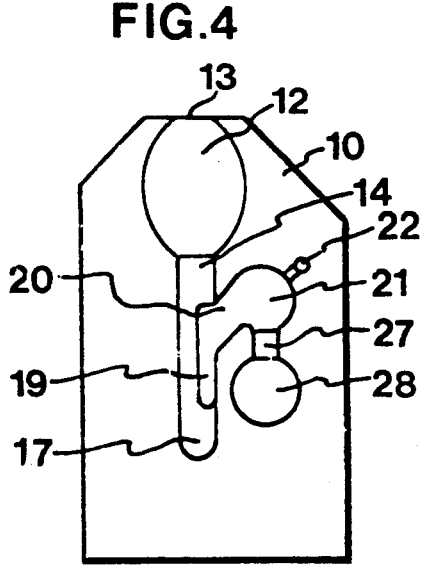
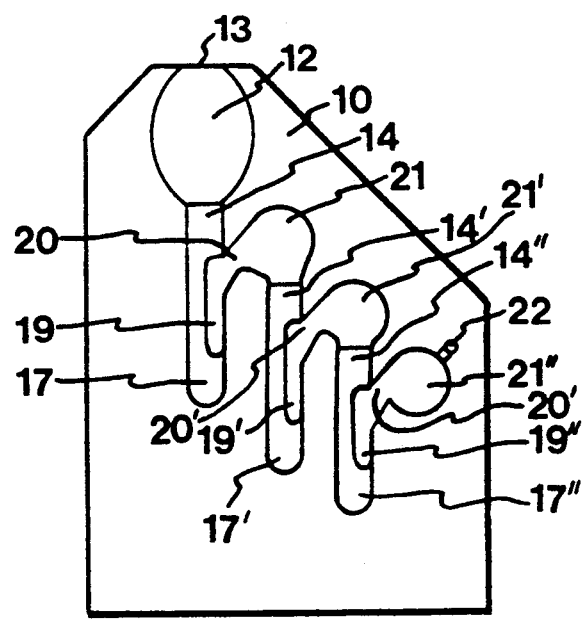

CUVETTE

The present invention relates to a cuvette for taking up at least one fluid and mixing the fluid with a reagent for analysing the mixture, the cuvette having at least one first cavity in which the fluid can be taken up through an inlet.

A cuvette of this type, which is used for direct optical analysis of the mixture, is previously known from U.S. Pat. No. 4,088,448. The cuvette according to this patent consists of a body member having two flat surfaces forming an optical path and spaced a predetermined distance from each other for determining the length of the optical path, and defining a cavity having an inlet by means of which the cavity communicates with the ambient atmosphere. The cavity has a predetermined fixed volume, and the predetermined distance between said surfaces enables the cavity to take up a sample by capillary action. Further, a reagent is applied to the surfaces of the cavity.

This known cuvette offers many advantages over other prior art apparatuses of the same type. By means of the cuvette, a fluid can be taken up, mixed and chemically reacted with a suitable reagent, e.g. for colour development in the same cavity as is used for the subsequent measuring operation. Thus, the cuvette according to U.S. Pat. No. 4,088,448 simplifies the sampling procedure, reduces the amount of accessory equipment and in most cases—depending on the type of analysis—considerably increases the accuracy of the analysis by making the analysis procedure independent of the skill of those carrying out the analysis.

The cuvette according to U.S. Pat. No. 4,654,197 increases the number of reactions possible in a cuvette system, by using a semipermeable membrane as a functional part of the cuvette.

The object of the present invention is to further improve these known cuvettes and to that end, the new cuvette is characterized in that it has, in addition to said first cavity, at least one second cavity adapted to take up fluid from the first cavity by capillary action without any external influence via a first channel having means for admitting fluid therein by external influence only, preferably by the exertion of centrifugal force, and that at least the second cavity contains a reagent or a fluid-modifying agent.

Thus, the cuvette according to the invention has at least two cavities defined by surrounding walls, viz. a first cavity or inlet cavity in which the fluid is taken up, preferably by capillary action through the inlet, and a second cavity in which the fluid can be taken up after centrifugation of the cuvette. Preferably, a reception cavity is provided which communicates with the first cavity through said channel. The reception cavity can be said to be divided into two sections, viz. a first, lower section for receiving heavy material taken up in the fluid, and a second, upper section forming the second cavity and serving as measuring cavity. Instead of relying on centrifugal force for fluid transport through the channel, it is also possible to exert a pressure on the fluid in the first cavity, which however presupposes a venting device. The walls of the cavities, the reception cavity and the channel, or a desired portion thereof, may be coated with reagent or the like, and an analysis can be carried out on fluid in both the first cavity and the second or the capillary section of the reception cavity, and also in the heavier-material section of the reception cavity.

From e.g. U.S. Pat. No. 4,462,964 and U.S. Pat. No. 4,714,590 it is previously known, in an analysis cuvette, to provide capillary orifices in the fluid path. As opposed to the arrangement according to the invention, these orifices however serve to prevent fluid transport until the cuvette is subjected to centrifugation. During centrifugation, the fluid is pressed through the capillary orifices into the analysis cells. The special means which in the cuvette according to the invention prevents fluid from entering the channel might be in the form of capillary orifices as in the known devices, but such orifices would probably not be more effective than the hydrophobic filter material used. The capillary device provided between the channel of the cuvette according to the invention and its second cavity performs its function without any external influence.

One advantage of the improved cuvette according to the invention is that it can be used for whole blood sampling even if the analysis must be performed on plasma or serum. Thus, the cuvette can be used for analyses within a much broader range than the cuvettes according to U.S. Pat. No. 4,088,448 and U.S. Pat. No. 4,654,197. Another major advantage over prior art cuvettes is that the use of the centrifugal force makes it possible to carry out different reactions in different cavities, thus allowing a period of incubation before the next reagent is used. Yet another advantage is that such material as is produced or used in a reaction, such as precipitated proteins or immunoaggregates, which might otherwise interfere with subsequent reactions or measurements, can be separated by centrifugation.

The cuvette can be manufactured from glass or polymeric material. It is also possible to manufacture it from many other materials, e.g. different types of semipermeable materials, like the cuvette according to U.S. Pat. No. 4,654,197, or optically transparent or non-transparent materials. The reagent, which is provided in at least one cavity, can be deposited by evaporation, freeze-drying, spraying, screen-printing or by other techniques.

The functional parts of the cuvette may vary depending on the fluid to be analysed and the type of analysis. If the inlet cavity should take up the fluid by capillary action, the distance between the cuvette walls must be less than 1 mm, and preferably 0.7 mm. If this is not the case, the capillary action must be brought about by other means than the walls, and the wall material must be wettable with the fluid or treated to be so. The volume of the inlet cavity depends on the need of fluid in the succeeding cavities and the amount of material to be separated by centrifugation. The channel connecting the first cavity to the second or the reception cavity has low capillary action, i.e. the distance between the walls exceeds 0.7 mm. The walls defining the channel may suitably be manufactured from non-wettable material or treated so as to be non-wettable. The channel may also contain non-wettable filtering material or other means for preventing spontaneous transport of fluid from the first cavity. Thanks to this arrangement, the amount of fluid taken up becomes fairly exact and can be determined by the manufacturing process. By a suitable design of the channel, it can also be used for mixing the fluid passing through it during the centrifugation and, as indicated above, may also be provided with a reagent.

Of the two reception cavity sections, the lower section has, as stated above, low capillary action between the walls, whereas the upper section has high capillary action. The upper section merges into the lower via a portion which can be referred to as a "wick". The "wick" may consist of capillary channels in the cuvette walls, but may also consist of a traditionally operating wick of a special design. Fluid is thus drawn from the lower section into the upper by capillary action as soon as the centrifugal force ceases acting.

The invention will be described in more detail hereinbelow with reference to the accompanying drawings schematically illustrating some embodiments.

FIG. 1 is front view of a basic embodiment of the invention,

FIG. 2 is a longitudinal section of this embodiment, and

FIGS. 3-8 are front views of other embodiments of the invention having different numbers of cavities and reception cavities of modified designs.

Figure 6:
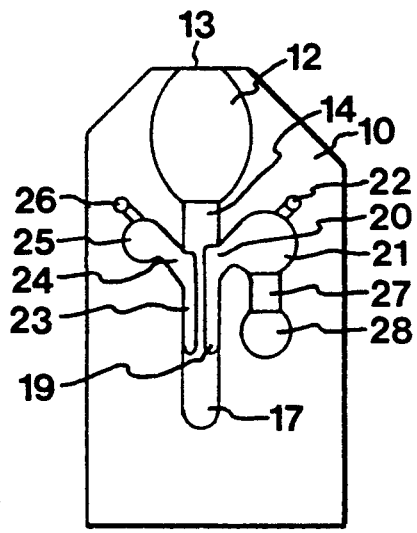

The cuvette in FIGS. 1 and 2 has a first wall 10 of glass or polymeric material and a second wall 11, also of glass or polymeric material. The walls 10 and 11 may also comprise several other materials, such as optical windows, semipermeable membranes, electrode material or other technical means. The walls 10, 11 define a plurality of cavities of different depths. A first cavity 12, or inlet cavity is adapted to take up a liquid sample and has such a depth that it can be filled by capillary action through a capillary inlet 13 communicating with the ambient atmosphere. However, it is also conceivable to fill this cavity by injecting the liquid sample, although one of the advantages of the invention will then be lost. The first cavity 12 may be provided with a reagent, that is an agent for reacting with the liquid sample drawn into the cavity. The reagent may be deposited on the walls of the cavity by evaporation, freeze-drying, spraying, screen-printing or in any other suitable way, depending on how the cuvette is manufactured. The first cavity 12 may also contain an agent otherwise modifying the sample. The first cavity 12 passes into a channel 14 which owing to its depth, as shown in FIG. 2, exerts low capillary action on the liquid received in the inlet cavity and has walls of hydrophobic material or walls treated with such a material. Further, the channel may also be provided with a hydrophobic filtering material, as shown at 15. These measures can also be combined. Further, the channel 14 may include a reagent or a modifying agent. The channel 14 opens into a reception cavity 16, 17 divided into two sections, viz. an upper section 16, which may also be referred to as "second cavity", and a lower section 17. The upper section or second cavity 16 exerts capillary action because of the small distance between the walls, as shown in FIG. 2, whereas the lower section 17, like the channel 14, does not exert any capillary action because of its greater depth. The walls of the lower section may be treated in the same way as the walls of the channel. Between the upper section or second cavity 16 and the lower section 17, there is provided a wick 18 connected to the upper section, but terminating at a certain distance from the bottom of the lower section. This "wick" 18 may be a conventional wick of any suitable material, but may also consist of special capillary slots in the cuvette walls or formations thereon.

When using the cuvette according to FIGS. 1 and 2, the first cavity 12 is filled with a liquid sample which in the illustrated embodiment is drawn into the cavity by capillary action through the inlet 13. The liquid sample mixes with reagent or the like provided in the cavity 12, and the mixture can then be analysed, e.g. in a photometer. If the cuvette is thereafter subjected to centrifugal force, the liquid sample or a portion thereof present in the cavity 12 can be caused to pass through the channel 14 and, during centrifugation, reach the lower section 17 of the reception cavity. When centrifugation thereafter ceases, a portion of the liquid sample will be drawn up into the upper capillary section 16 by means of the wick 18. Since the wick 18 does not reach as far as the bottom of the lower section 17, heavier material will remain therein, thus allowing separation of material. The volumes of the different cavities or sections must be so related to each other and to the volume of heavier material taken up or produced in the liquid sample, that no part of the cuvette will be excessively filled or receive an insufficient amount of fluid. Depending on the analysis to be made, neither, one or both of the sections 16, 17 can be provided with a reagent or a modifying agent. An analysis can then be made on the liquid in the upper section 16 and also on the heavier material in the lower section 17. Examples of heavier material are blood cells collected in the section 17 when analysing a blood sample.

FIG. 3 shows an embodiment of the invention which is more useful in practical application. The cuvette may be designed in the same way as in FIGS. 1 and 2 and has a first cavity 12 with an inlet 13, a channel 14 with hydrophobic obstacles and a reception cavity 17. However, the upper section or second cavity, here designated 21, of the reception cavity is offset with respect to a centre line passing through the first cavity and the lower section of the reception cavity 17. The second cavity 21 communicates with the reception cavity 17 by a capillary channel 20 making an angle with the centre line passing through the first cavity 12 and the reception cavity 17. A capillary formation or wick 19 of the same type as the wick 18 is connected with one end to the Capillary channel 20 and extends a certain distance downwards towards the bottom of the section 17, but terminates at a safe distance therefrom for the same reason as in the previous embodiment. The second cavity 21 is here connected to a venting device in the form of a channel 22 opening into the ambient atmosphere for preventing the formation of air inclusions. In this cuvette, the measuring or reaction cavity 21 is thus not located in the fluid path existing during the centrifugation of the cuvette and may thus be provided with a reagent incompatible with the heavier material in the liquid. This simple cuvette solves a number of analysing problems. Reagents or other agents can be deposited in several places by different techniques. Incubations over suitable times are possible in the first cavity 12 and in the reception cavity 17 during centrifugation and, of course, in the second cavity 21. If several reagents or the like are required on different occasions after a separation process, the cuvette must have more than three cavities, where a second cavity serves as an inlet cavity for a new cycle of centrifugation, as will appear from the following description.

The cuvette in FIG. 4 thus has a second reception cavity 28 communicating with the second cavity 21 through a channel 27 which, like the channel 14, is provided for Preventing spontaneous liquid transport by capillary action. The second reception cavity 28 r-an be used as a further measuring cavity and may be provided with a reagent or the like. Liquid present in the second cavity 21 can be caused by centrifugation to pass through the channel 27 to be taken up in the reception cavity 28. After a predetermined time and optionally after mixing with a reagent, the liquid can be subjected to analysis in the cavity 28. One of the advantages of this embodiment of the invention is that a reagent can be provided in the cavity 21 and the liquid received there passed, after a predetermined time of incubation, to the reception cavity 28 after centrifugation of short duration, and the liquid is then mixed in the cavity 28 with a new reagent or the like in order to be analysed after a predetermined time of incubation.

FIG. 5 shows an embodiment which, in addition to the first cavity 12, the channel 14 and the reception cavity 17, has a second cavity 21, a third cavity 21' and a fourth cavity 21" as well as a second channel 14' and a third channel 14", a second reception cavity 17' and a third reception cavity 17" as well as a first capillary channel 20, a second capillary channel 20' and a third capillary channel 20". A liquid taken up in the first cavity 12 is passed, as described above, into the reception cavity 17 by centrifugation, from where it is taken up in the second cavity 21 by capillary action through the wick 19 and the capillary channel 20. From the second cavity 21, the liquid is transported to the reception cavity 17' via the channel 14', also by centrifugation, to be drawn from there up into the third cavity 21' by means of a wick 19' in the same manner as in the preceding step. Similarly, the liquid is taken up in the fourth cavity 21" via the reception cavity 17", the wick 19" and the channel 20". There are not very many analyses having such a complicated reaction pattern as to necessitate a cuvette of the embodiment now described. However, this embodiment clearly shows the versatility of the invention. In the last-mentioned embodiment, the venting channel 22 is connected to the last cavity 21" in the series of cavities.

FIG. 6 shows a further embodiment which is a combination of the embodiments of FIGS. 3 and 4. Thus, to a reception cavity 17 are connected two channels 20, 24 which are each connected to a second cavity 21, 25 and each have a wick 19, 23. The cavities 21, 25 each have a venting channel 22 and 26, respectively. The embodiment in FIG. 6 can be used for performing two analyses which must be carried out after different times of incubation. Since two analyses can be performed after a single centrifugation, the cuvette according to FIG. 6 can be time-saving in many cases.

One practical example of the versatility of the invention is the analysis of urea and alkaline phosphatase from whole blood in the cuvette according to FIG. 6. The cuvette wall 10 with the recesses defining the cavities can be manufactured from cellulose-based resin while the other wall, forming a lid, can be cut from a sheet of the same material.

The surfaces of the cavities depending on capillary force can be treated by corona discharge or in any other way for increasing wettability. The hydrophobic channels 14, 14', 14" and 27 can be treated with silicone fluid, and a filter consisting of a small piece of sintered polypropylene can be pressed into place in the upper part of these channels. A mixture of glycine, magnesium chloride, paranitrophenyl phosphate and a carrier agent, giving a pH of 10.5 when dissolved in plasma, is printed on one or both of the large surfaces defining the second cavity 21. On the surfaces defining the cavity 28 in FIG. 6 is printed a mixture of sodium hydroxide and a carrier agent. To one of the walls defining the cavity 25 is applied a mixture of urease and an alkaline buffer, and on the corresponding area of the opposite wall is applied a substantially transparent material of cellulose ester containing a pH indicator with an indicator range within the acid area. The first cavity 12 and the reception cavity 17 may contain heparin to prevent coagulation If the reaction time is long. The two walls which according to FIG. 2 form the cuvette can be joined together by welding or gluing. Both methods give excellent results.

In the use of a cuvette according to FIG. 6, which has been treated in the manner just described, the cuvette is contacted with a whole blood sample and placed in a special centrifuge photometer. Centrifugation is started, and the blood is passed into the reception cavity 17. After 60-90 seconds, the blood cells have been separated, and the centrifuge is stopped. Plasma is now drawn up into the cavities 21 and 25 through the channels 20 and 24. The photometer may have an initial measurement as reference, otherwise analysing starts by monitoring the kinetic turnover or reversal of the pH indicator because of the ammonia produced by the urease action on the sample urea in the cavity 25. As the urea value is read, the alkaline phosphatase reaction proceeds in the second cavity 21 and after a predetermined time, the centrifuge is started in order, after a short time, to bring the reaction to a stop when the liquid has been contacted with the sodium hydroxide in the cavity 28, which also develops a yellow colour of digested substrate. After measuring the colour in the cavity 28, the data received is processed and the analytical values are presented.

Figure 7:
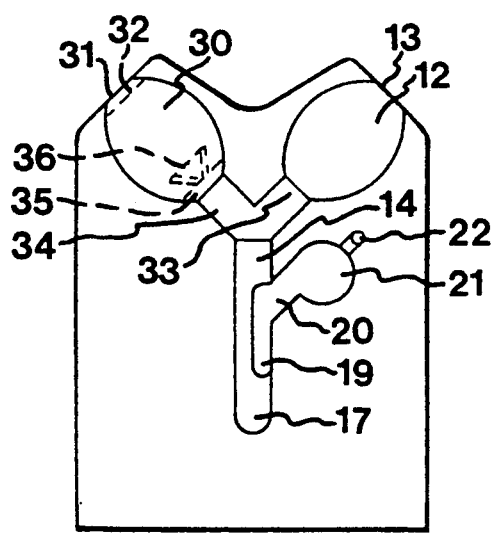

It may sometimes be desirable to dilute or wash the drawn-up fluid with a liquid which should be applicable in one or more cavities provided therefor. To this end, a cuvette of the design shown in FIG. 7 can be used. Here, the cavity 12 is connected in parallel with a cavity 30 for taking up said liquid. The two cavities 12 and 30 each have an outlet channel 33 and 34, respectively, both of which open in the channel 14. During centrifugation, fluid and liquid in the cavities 12 and 30, respectively, will flow into the channel 14 and through this channel into the reception cavity 17 and so forth, as in the preceding embodiments.

The diluting or washing liquid can be sucked into the cavity 30 in connection with the analysis, but it can also be supplied in advance, suitably when applying the reagent, in which case the liquid must be sealingly enclosed, which can be done by means of sealing plugs or membranes provided in the inlet and the outlet of the cavity. It is also conceivable to place a capsule of suitable material in the cavity 30. When the cuvette is to be used, the two seals can be penetrated by means of a suitable tool. It is also possible, as illustrated at 36, to provide some type of perforation means 36 in the cavity. When the cuvette is subjected to centrifugation, the perforation means 36 will thus be urged into engagement with the seal 35 in the outlet so as to penetrate it.

Figure 8:
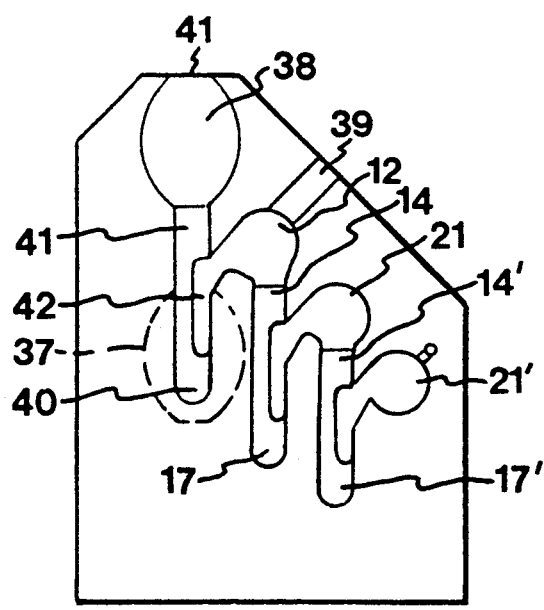

It is also conceivable to connect the cavity with washing or diluting liquid in series with the fluid reception cavity 12. This can be done, for instance, by modifying the cuvette according to FIG. 5 in the way shown in FIG. 8. The cavity, which in the embodiment according to FIG. 5, serves as second cavity 21 is here used as first cavity 12 by being provided with an inlet 39. The first cavity in FIG. 5 here forms a cavity 38 for receiving diluting or washing liquid which, like the fluid in the embodiments described above, is supplied by means of a channel 41, a reception cavity 40 and a liquid-drawing capillary formation 42, to the fluid reception cavity 12 and transported, if so desired, to the succeeding cavities in the same manner as in the embodiment of FIG. 5. The diluting or washing liquid can be drawn into the cavity 38 by capillary action in connection with the analysis, but many times it is instead more conveniently applied in advance and sealingly enclosed in the cavity in the same manner as in the cavity 30 in FIG. 7.

In certain analyses, it may be desirable to retain part of the fluid or the diluting or washing liquid which by the centrifugation has reached the respective reception cavity 17 and 40, in this cavity. Suitably, the cavity is widened, as shown at 37, so as to have a volume exceeding the volume of the cavity 21 and 12, respectively. After a second centrifugation, in which e.g. the cavity 21 has been emptied, fluid is therefore again drawn up from the cavity 17.

The drawings show all the cavities as defined by sealing walls, but it is evident that one or some of these walls can be replaced by a semipermeable membrane, as stated in U.S. Pat. No. 4,654,197.

The invention will be further illustrated by Examples 1 and 2, relating to the determination of hemoglobin and glucose in whole blood, and glucose and protein in serum or plasma, respectively, using the cuvette described above.

EXAMPLE 1

Determination of Hemoglobin and Glucose in Whole Blood

The red cells of the blood, the erythrocytes, carry inside their semipermeable membrane, primarily of lipides and proteins, a plurality of water-soluble chemical substances of both low- and high-molecular type. An example of the high-molecular type is the oxygen-transporting protein hemoglobin and an example of the low-molecular type Is glucose which is a necessary energy substance for sustaining metabolism. Low-molecular substances often exist both intra- and extracellularly, while high-molecular substances often cannot pass through the membrane of the erythrocytes. When determining hemoglobin or glucose in whole blood, the membrane of the erythrocytes is ruptured, e.g. by a detergent or an osmotic shock or a combination thereof, and the substances contained in the erythrocytes become available for chemical analysis.

Hemoglobin

In a cuvette according to the invention, e.g. FIG. 3, the cavity 12 is supplied with a dry chemical reagent consisting of 0.30 mg sodium deoxycholate
0.15 mg sodium azide
0.15 mg sodium nitrite
0.1 mg non-reactive ingredients The reagent composition for a certain cuvette quantity is dissolved in a small amount of water and Pluronic P85 ®. The reagent composition has such a viscous consistency that it can be uniformly applied over the surface in the cavity 12, e.g. by screen-printing or dabber printing. The reagent Composition used produces, together with hemoglobin, a hemoglobin azide complex which can be determined photometrically in the cavity 21. The cuvette with hemoglobin reagent is used such that the cavity 12 is supplied with whole blood. The reagent dissolves into the blood, and the chemical reaction forming a hemoglobin azide complex is finished after about 45 seconds. The contents in the cavity 12 are transferred, e.g. by centrifugal force, into the cavity 21 where a clear low-turbid solution can be analysed by photometry. The distance between the walls in the cavity 21 is about 0.13 mm.

Glucose 1 kU GDH, glucose dehydrogenase
220 U NAD
0.3 mmol MTT
250 g White Saponin ®
50 mg Pluronic P85 ®
250 µl water subjected to ion-exchange The components included are finely divided into a suspension which is suitable to be used for coating surfaces by different printing techniques, such as silk screen printing, cylinder printing etc. This type of suspension is suitable for coating cuvettes according to the invention. In certain cases, surface-tension reducing substances may be added for facilitating the coating of hydrophobic plastic materials. In order to adapt the suspension to different coating equipment, the viscosity can be varied by adding suitable high-molecular polymers. The choice of high-molecular polymers is not critical, but affects the dissolving rate of the dry reagent. Among usable polymers may be mentioned polyethylene glycol, polyvinyl pyrrolidone, dextran and different cellulose derivatives. The choice of polymer can also be made with a view to stabilising the suspension. On the basis of known preparation techniques in e.g. the foodstuffs or cosmetics industry, the reagent can be adapted to different surfaces.

The reagent for glucose in whole blood is placed, as described above, in a cuvette according to the invention of the type shown in FIG. 3. The glucose reagent is placed in the cavity 12. The transfer of reagent into the cavity 21 can be achieved, e.g. by centrifugal action. The cavity 12 is filled with whole blood, and the glucose reagent brings about a conversion of glucose into a photometrically measurable colour at end-point after about 3 minutes. The transfer into the cavity 21 can be effected after the red blood cells, the erythrocytes, have been ruptured, i.e. about 1 minute after. In the same way as in the case of hemoglobin, photometering is carried out in a low-turbid clear aqueous solution. The distance between the walls in the cavity 21 is about 0.14 mm for glucose determination in whole blood. The photometric method for determining glucose and hemoglobin in whole blood is advantageously performed by a two-wavelength measurement.

EXAMPLE 2

Determination of Glucose and Protein in Serum or Plasma

When determining an analyte in plasma or serum, the red blood cells, the erythrocytes, should be excluded. A cuvette according to the invention is especially well suited for analysing in plasma or serum when the cuvette has several cavities and the communication between the different cavities is maintained by capillary force and centrifugal force. Blood is drawn into a cavity, often by capillary force by direct sampling, and plasma or serum is transferred, after centrifugation of the cuvette, by capillary force into a cavity containing a reagent composition, specifically suited for determining the analyte.

Glucose in Plasma or Serum

Reagent composition, 1 ml:

1 kU GDH, glucose dehydrogenase enzyme
220 U NAD
0.3 mmol MTT
50 mg Pluronic P85 ®
250 µl water subjected to ion-exchange The reagent chemicals included are treated as in the previous Example for determining glucose in whole blood. Any modification of the reagent composition to achieve an adequate function, such as dry reagent, and adhesion to the walls of the cuvette cavity complies with the description in the previous Example.

For determining glucose in plasma or serum in a cuvette according to the invention, the cuvette according to FIG. 3 is advantageously used. The reagent composition described above is applied in the cavity 21, e.g. by printing technique, uniformly over the surface thereof. After drying, the reagent passes into what is often referred to as dry reagent. A lid is placed over cavities and other channels in the structure. Whole blood is sampled and flows into the cavity 12, e.g. by capillary action. After sampling, the cuvette is centrifuged, and after completed centrifugation the cavity 21 is filled with plasma or serum by capillary action. The red blood cells have been removed by centrifugation and cannot fill the cavity 22. A-he reagent composition dissolves in serum or plasma, and the chemical reaction permits a specific determination of glucose. The chemical reaction, i.e. the glucose content, can be read directly in the cuvette by photometric technique.

Protein in Serum or Plasma

Reagent composition:
1 mmol lithium tartrate
1 mmol copper tartrate
7 mmol lithium hydroxide These chemical substances are dissolved in a suitable amount of water. In order that the solution should be given the correct viscosity for application in a cavity by printing technique, the solution is evaporated. The application of the reagent by printing technique is facilitated if the dry reagent additionally contains about 0.5-2% lithium lauryl sulphate and about 1-5% polyvinyl pyrrolidone/polyvinyl acetate copolymer and optionally a plasticiser.

The reagent is applied in the cavity 21 in a cuvette according to FIG. 3. The cuvette functions in the same manner as the cuvette used for glucose determination in plasma or serum.

The cuvette according to the invention can be used for many types of analyses and is especially well suited for routine-type blood analyses, such as determination of glucose, urea-nitrogen in blood, albumin, bilirubin, total protein etc., particularly on the basis of whole blood, and for a large number of other analyses. Thus, the invention must not be considered restricted to what has been described above, but may be modified in several different ways within the scope of the accompanying claims.

We claim:

1. A cuvette for taking up at least one fluid and for mixing a fluid with a dry reagent for analyzing a mixture, wherein said cuvette comprises:
   a) at least one capillary first cavity having an inlet and constructed and arranged to take up a fluid by capillary action alone;
   b) a first channel having a non-capillary and non-spontaneous fluid transporting function operative only under external influence by application of a centrifugal force on the cuvette;
   c) a centrifugation reception cavity communicating with said at least one capillary first cavity via said first channel and constructed and arranged to exert no capillary action:
   d) at least one capillary second cavity constructed and arranged to take up fluid by capillary force alone; and
   e) a first capillary transporting means projecting into said centrifugation reception cavity, being connected to said at least one capillary second cavity and constructed and arranged to transport fluid by capillary action from said centrifugal reception cavity into said at least one capillary second cavity.

2. A cuvette as claimed in claim 1, further comprising a capillary channel provided between said reception cavity and said at least one capillary second cavity, an end portion of said first capillary transporting means facing away from said reception cavity being fixed in said capillary channel.

3. A cuvette as claimed in claim 1, further comprising a second reception cavity communicating with said at least one capillary second cavity via a second channel corresponding to said first channel.

4. A cuvette as claimed in claim 3, wherein said second reception cavity has a second capillary transporting means corresponding to said first capillary transporting means and connected to a second capillary channel opening in a capillary third cavity.

5. A cuvette as claimed in claim 4, further comprising at least a third reception cavity, a third channel, a third capillary transporting means, a third capillary channel and a capillary fourth cavity connected to said at least one capillary second cavity via said capillary third cavity.

6. A cuvette as claimed in claim 5, having a plurality of channels and reception cavities, and capillary transporting mans, capillary channels and cavities, wherein all channels and reception cavities extend along parallel lines making an angle with parallel lines along which the capillary channels extend.

7. A cuvette as claimed in claim 1, wherein at least two capillary cavities are connected to each reception cavity.

8. A cuvette as claimed in claim 1, wherein said capillary transporting means consists of a wick.

9. A cuvette as claimed in claim 1, wherein all cavities and/or reception cavities are coated with reagents or fluid-modifying agents.

10. A cuvette as claimed in claim 1, wherein at least one cavity for receiving diluting or washing liquid is connected in parallel with said at least one capillary first cavity, said two cavities having outlets connected to said first channel.

11. A cuvette as claimed in claim 1, wherein at least one cavity for receiving diluting or washing liquid is connected in series with said at least one capillary first cavity via a channel, a reception cavity and a capillary transporting means.

12. A cuvette as claimed in claim 10, wherein said cavity for receiving diluting and washing liquid is provided, at an inlet and an outlet thereof, with means for sealingly enclosing a liquid, the means for sealingly enclosing the liquid provided in said outlet being rupturable by a penetrating means disposed in the cavity and activatable by centrifugal force.

13. A cuvette as claimed in claim 1, wherein at least one reception cavity has a larger volume than the succeeding cavities which are arranged to take up fluid from said reception cavity.

14. A cuvette as claimed in claim 1, wherein at least one of the cavities is covered with a hydrophillic or hydrophobic semipermeable membrane containing a reagent.

15. A cuvette as claimed in claim 1 in which said capillary second cavity is offwet with respect to said first channel and wherein said capillary second cavity communicates with the ambient atmosphere through a vent.

16. A cuvette as claimed in claim 1 in which said capillary second cavity is in line with said first channel and between said first capillary cavity and said centrifugation reception cavity.

17. A cuvette as claimed in claim 1 wherein said capillary second cavity contains a dry reagent or a fluid-modifying agent.

* * * * *